United States Patent

Sanders et al.

[11] Patent Number: 5,871,548
[45] Date of Patent: Feb. 16, 1999

[54] MODULAR ACETABULAR REINFORCEMENT SYSTEM

[75] Inventors: Anthony P. Sanders, Lakeville, Mass.; Ian Revie, New Milton, United Kingdom; Alan Cornell, Franklin, Mass.; Allan E. Gross, Toronto, Canada

[73] Assignee: Johnson & Johnson Professional, Inc., Raynham, Mass.

[21] Appl. No.: 762,885

[22] Filed: Dec. 7, 1996

[51] Int. Cl.⁶ .................................................. A61F 2/32
[52] U.S. Cl. .................................. 623/22; 623/23; 606/71
[58] Field of Search .......................... 623/22, 23; 606/71

[56] References Cited

U.S. PATENT DOCUMENTS

| | | | |
|---|---|---|---|
| 4,623,353 | 11/1986 | Oh | 623/23 |
| 4,792,337 | 12/1988 | Müller | 623/22 |
| 4,871,368 | 10/1989 | Wagner | 623/22 |
| 4,936,861 | 6/1990 | Muller et al. | 623/22 |
| 4,959,072 | 9/1990 | Morscher et al. | 623/22 |
| 5,156,625 | 10/1992 | Marchetti et al. | 623/22 |
| 5,192,329 | 3/1993 | Christie et al. | 623/22 |
| 5,314,490 | 5/1994 | Wagner et al. | 623/22 |
| 5,326,367 | 7/1994 | Robioneck | 623/22 |
| 5,326,368 | 7/1994 | Collazo | 623/22 |
| 5,425,778 | 6/1995 | Zichner et al. | 623/22 |
| 5,487,743 | 1/1996 | Laurain et al. | 606/71 |
| 5,507,828 | 4/1996 | Maumy et al. | 623/22 |
| 5,702,474 | 12/1997 | McCandliss | 623/23 |
| 5,702,477 | 12/1997 | Capello et al. | 623/22 |

FOREIGN PATENT DOCUMENTS 0295912  4/1992  European Pat. Off. .

OTHER PUBLICATIONS

P. Haentjens, et al., *The Müller acetabular support ring A preliminary review of indications and clinical results*, Orthopaedics & Traumatology, Academic Hospital V.U.B., Laarbeeklaan 101, B–1090 Brussels, Belgium, 1986, pp. 223–230.

Daniel J. Berry, et al., *Revision Arthroplasty Using an Anti–Protrusio Cage for Massive Acetabular Bone Deficiency*, British Editorial Society of Bone and Joint Surgery, 0301–620X/92/5439, Sep. 1992, vol. 74–B, No. 5, pp. 711–715.

M.E. Müller, *Self–Locking System SLS–88*, PROTEK AG Erlenauweg 17, P.O. Box 3119 Münsingen–Berne, Switzerland, Ref. No. 91.29.03, 1993, pp. 1–42.

J. Schatzker, et al., *A Preliminary Review of the Müller Acetabular and Burch–Schneider Antiprotrusio Support Rings*, Archives of Orthopaedic and Traumatic Surgery, 1984, 103:5–12, pp. 5–12.

*Primary Examiner*—Paul B. Prebilic
*Attorney, Agent, or Firm*—Nutter, McClennen & Fish, LLP

[57] ABSTRACT

A modular acetabular reinforcement system includes a substantially cup-shaped reinforcement body having a peripheral flange portion. One or more fixation wings, of various sizes and shapes, are selectively and separately attachable to the flange portion of the reinforcement body. The system is mountable within the acetabulum of a patient to reinforce the acetabulum and to serve as a platform for other prosthesis components such as an acetabular shell.

24 Claims, 4 Drawing Sheets

MODULAR ACETABULAR REINFORCEMENT SYSTEM

CROSS REFERENCE TO RELATED APPLICATIONS

Not applicable.

STATEMENT REGARDING FEDERALLY SPONSORED RESEARCH

Not applicable.

BACKGROUND OF THE INVENTION

The invention relates to implantable prostheses, and more particularly to components of hip joint prostheses.

The hip joint is a ball-and-socket type joint in which the ball-shaped femoral head is engaged with and articulates with a cup-shaped socket known as the acetabulum. Injury and/or disease may damage the hip joint to the extent that it must be replaced by or augmented with a prosthetic joint. Deterioration of the acetabulum, and particularly the cartilage within the acetabulum, requires that a prosthetic acetabular shell be mounted within a prepared area of the acetabulum. The acetabular shell receives and articulates with a prosthetic femoral head which is installed on a proximal portion of a patient's femur.

In some instances, degenerative bone conditions deteriorate the acetabulum, and particularly its medial wall, to the extent that the acetabulum does not have the integrity to serve as a mounting platform for a prosthetic acetabular shell. This condition requires a reinforcement prosthesis which is implanted within the acetabulum before the acetabular cup, and at least a portion of which receives the acetabular cup. Such a reinforcement body, sometimes known as a protrusio cage, includes a main body that is at least partially cup-shaped and which includes two or more integral radially extending flanges. The protrusio cage is first stabilized within the acetabulum using bone cement or bone screws. Thereafter, the flanges are joined to the ilium, ischium and pubis to further secure the cage and to distribute forces away from the medial wall of the acetabulum. An exemplary protrusio cage is further described by Oh et al., Clin. Orthopaedics and Related Research, No. 162, pp. 175–184 (1982) and by Schatzker et al., Arch. Orthop. Traum. Surg., Vol. 103, No. 1, pp. 5–12 (1984). U.S. Pat. Nos. 4,437,193 and 4,623,352 also describe exemplary protrusio cages.

While known protrusio cages can be useful, they are often difficult to install in an ideal manner due to natural anatomical differences among patients as well as anatomical differences resulting from different disease and/or injury conditions. Because of these anatomical differences, the fixed flanges of known protrusio cages must be manipulated and/or altered, during surgery, to properly install the protrusio cage. Even with such manipulation and alteration, the protrusio cages still may not be optimally implanted within some patients.

Accordingly, there is need for protrusio cages, or similar acetabular reinforcement bodies, that can be more easily installed by surgeons during hip arthroplasty procedures to accommodate the varying anatomies of patients.

BRIEF SUMMARY OF THE INVENTION

The invention provides a modular reinforcement system which can be used to augment structural weaknesses of the acetabulum caused by degenerative conditions. The reinforcement system serves as a platform upon which known hip prosthesis components, such as an acetabular shell, can be mounted.

The modular acetabular reinforcement system comprises a reinforcement body, which can be substantially cup-shaped, having dome and rim ends and at least one peripheral flange portion extending along at least a portion of the perimeter of the rim end. The dome end is inserted within the acetabulum while the peripheral flange of the rim end mounts adjacent to the acetabular lip. The system further comprises at least one attachable fixation wing that is separately attachable to the reinforcement body. Each fixation wing has a first end that is attachable to the peripheral flange portion of the reinforcement body and an opposed, second end which can be affixed to bone adjacent the acetabulum. The fixation wing includes at least one bone fixation hole disposed therein that can accommodate bone screws or the like to assist in securing the reinforcement body to portions of the patient's pelvic bone. The reinforcement body itself may include one or more holes disposed therein to assist in affixing, or partially affixing, the reinforcement body to the acetabulum. Optionally, bone screws may be inserted through the holes in the reinforcement body to assist in mounting or stabilizing the reinforcement body within the acetabulum. In some instances the use of bone screws can be avoided and initial fixation of the reinforcement body within the acetabulum can be accomplished using bone cement.

The flange portion of the reinforcement body may include one or more fixation holes that can cooperate with similar fixation holes disposed on the first end of the fixation wing so that screws, rivets, or other fixation elements can selectively join one or more fixation wings to the reinforcement body.

The system may include one or more fixation wings, and the fixation wings can be provided in different sizes and shapes.

The reinforcement system of the invention can be utilized by first preparing the acetabulum and then inserting the reinforcement body within the acetabulum in an appropriate position and orientation as required by the patient's anatomy. The initial fixation or stabilization of the reinforcement body within the acetabulum can be effected using bone screws or bone cement. The surgeon then selects from among a variety of differently sized and shaped fixation wings, depending on the anatomy and bone condition of a given patient, so that one or more suitable fixation wings is selected. The first end thereof is attached to the flange portion of the reinforcement body through an appropriate fixation technique. Any necessary manipulation or alteration of the fixation wing can be effected, and the second end of the fixation wing is then affixed to bone within the pelvic area of the patient. In most instances the second ends of the fixation wings are attached to the ilium and ischium and the pubis of the patient in order to properly secure the reinforcement body and to create desirable force transfer away from the medial wall of the acetabulum. It is understood that the steps noted above are intended to be exemplary and that surgeons may well deviate from the procedure noted above. For example, it may be desirable to assemble the fixation wings prior to placing the reinforcement body.

DETAILED DESCRIPTION OF THE INVENTION

Figure 1:
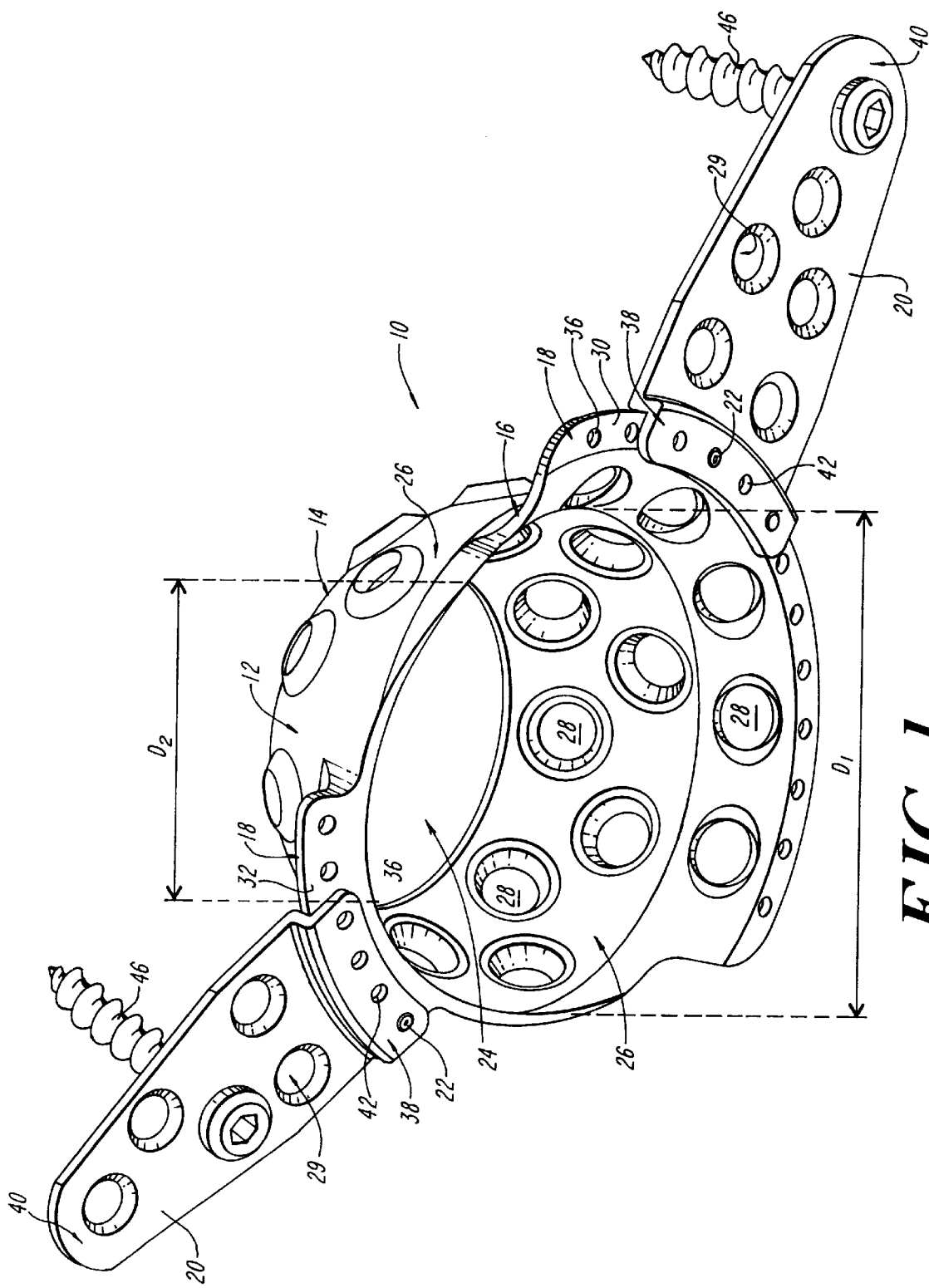
FIG. 1 is a perspective view of an acetabulum reinforcement system constructed according to the present invention.
Figure 2:
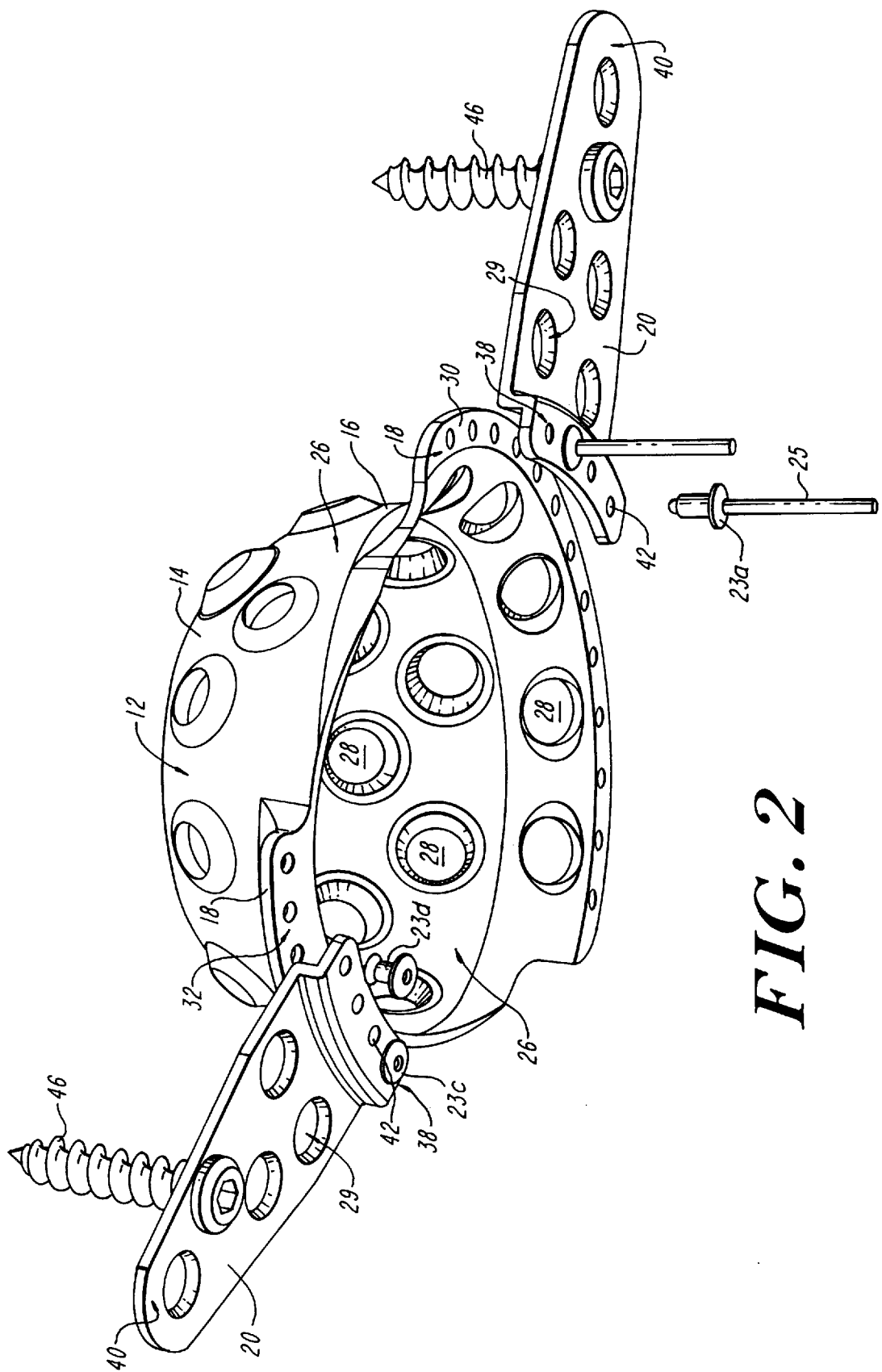
FIG. 2 is an exploded view of the modular acetabular reinforcement system of FIG. 1.
Figure 3:
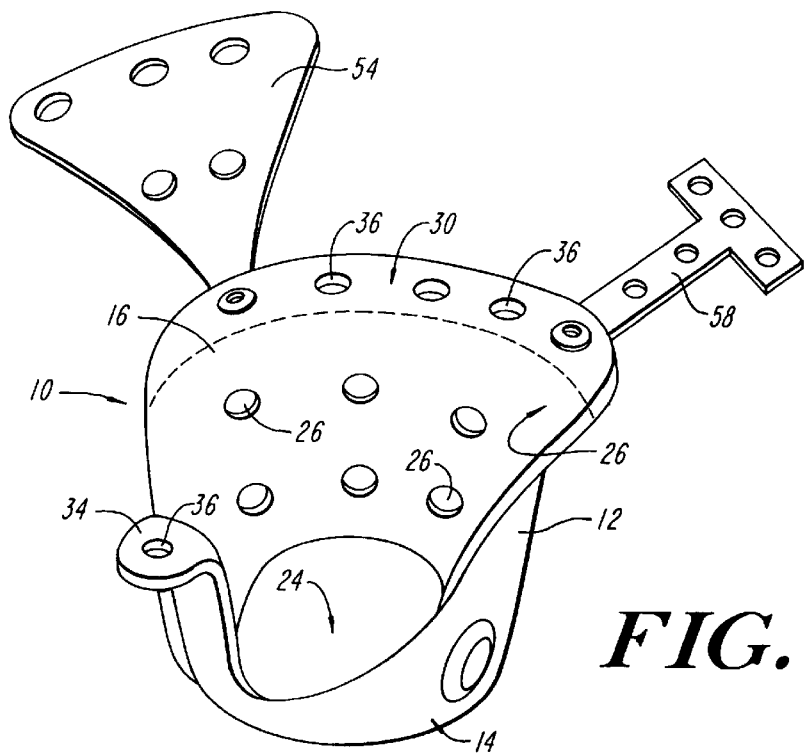
FIG. 3 is a perspective view of an alternative embodiment of a modular acetabular reinforcement system according to the present invention.

Referring to FIGS. 1–3, the acetabular reinforcement system 10 of the invention includes a reinforcement body 12, which is substantially cup-shaped. The body 12 has dome 14 and rim 16 ends, and a peripheral flange portion 18 is formed as a part of the rim end. One or more fixation wings 20 are selectively and separately attachable to flange portion 18. In one embodiment, fixation elements 22, such as screws or rivets and the like, can be used to secure the fixation wings 20 to the flange portion 18.

Figure 5:
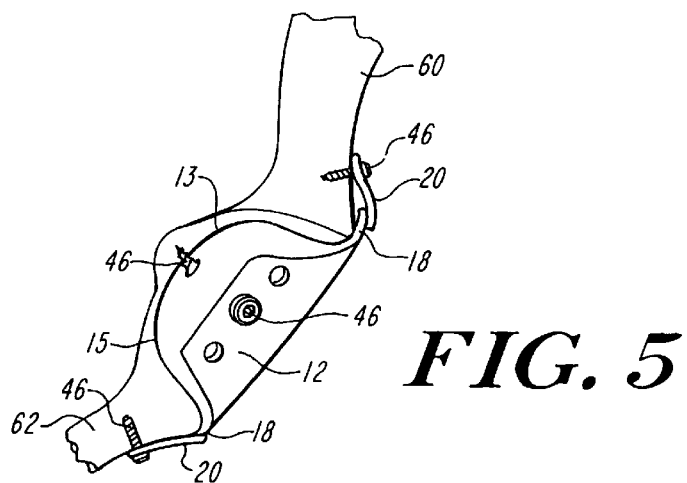
FIG. 5 is a sectional view of an acetabulum having mounted therein a reinforcement system according to the present invention.

The reinforcement body, as illustrated in FIGS. 1–3, may have an open dome end 14, represented by apical hole 24. Alternatively, as illustrated in FIG. 5, the dome end 14 may be closed to form a roof-like structure 13 for the reinforcement body. The rim end 16 must be open and should be of suitable dimensions to receive an acetabular shell (not shown) of known structure.

The structure sidewall 26 of reinforcement body 12 preferably is at least partially dome-shaped such that the nominal diameter ($D_1$) of the opening at rim end 16 is greater than the nominal diameter ($D_2$) of the opening at the dome end 14. Structural sidewalls 26 preferably include countersinks 28 which can accommodate bone screws or, alternatively, encourage bone-growth. Flange 18 can be formed in a continuous manner (not illustrated) about the perimeter of the rim end of the reinforcement body 12. As illustrated in FIGS. 1–3, flange 18 preferably is discontinuous. FIGS. 1 and 2 illustrate a reinforcement body in which flange 18 includes superior-lateral flange 30 and a smaller, inferior-medial flange 32. FIG. 3 illustrates a reinforcement body in which flange 18 includes superior-lateral flange 30 and an inferior-medial flange tab 34. Preferably, the flange 18 includes holes 36 that can assist in affixing the fixation wings to the reinforcement body.

The fixation wings 20 include a first end 38 and an opposed second end 40. Fixation holes 42 preferably are formed on the first end 38 of the fixation wings 20. Holes 42 should be of a size and shape such that they are suitable to cooperate with holes 36 disposed in flange portion 18. Fixation elements 22, such as screws, rivets, and the like, can be inserted through holes 36 and 42 to selectively join fixation wings 20 to the reinforcement body 12.

The body portion 44 of the fixation wing preferably includes one or more countersinks 29 that can be used to seat bone screws 46 to secure the fixation wings 20 to portions of bones within the pelvis of a patient.

A variety of fixation techniques can be used to selectively join fixation wings 20 to reinforcement body 12. For example, the fixation elements 22 can be such that they include a combination of nuts and bolts that firmly and selectively secure the fixation wings to the reinforcement body. Alternatively, a crimping tool (not shown) can be used to deform the interfacing portions of the fixation wings 20 and the flange portion 18 in order to create an interlocking mechanical engagement of these elements.

FIG. 2 illustrates an embodiment in which the fixation elements 22 are rivets 23. Rivet 23a is an unassembled, unactuated rivet including mandrel portion 25. Adjacent rivet 23a is rivet 23b which is assembled within the fixation wing, but which is not actuated. FIG. 2 also illustrates rivet 23c which is assembled and actuated within a hole 42 of fixation wing 20. Rivet 23d is an example of an actuated rivet exploded from hole 42.

Figure 7:
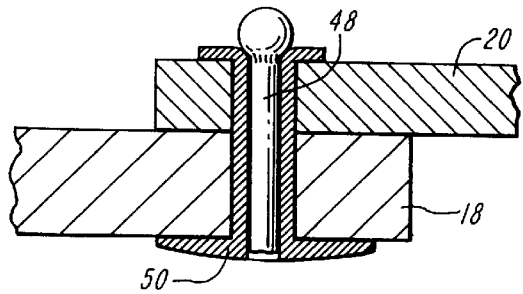
FIG. 7 illustrates an exemplary rivet connection that is utilized to join a fixation wing to the reinforcement body.

FIG. 7 illustrates a rivet connection in which rivet components 48 and 50 cooperate to secure the flange 18 and the fixation wing 20 to each other. Although FIGS. 1 and 2 illustrate the use of two fixation elements to secure each fixation wing 20 to flange 18, it is understood that it may be desirable to use only one fixation element to enable pivotal movement of the fixation wing with respect to the reinforcement body to accommodate anatomical differences among patients. Alternatively, more than two fixation elements can be used to secure a single fixation wing to flange 18.

Figure 4A:
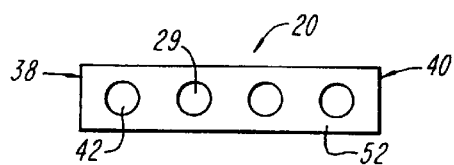
FIGS. 4A–4D illustrate various designs of fixation wings useful with the system of the present invention.
Figure 4B:
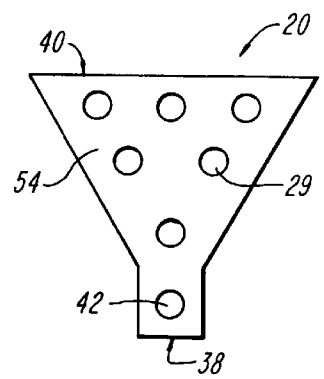
Figure 4C:
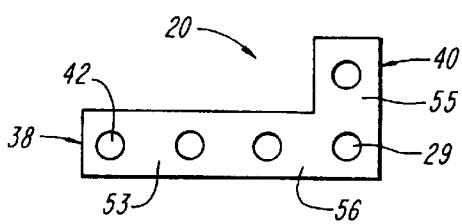
Figure 4D:
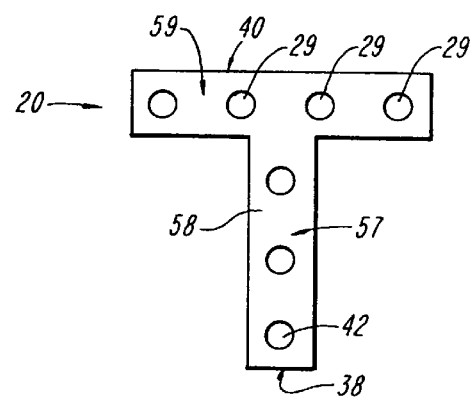

FIGS. 4A–4D illustrate various shapes in which fixation wing 20 can be created. FIG. 4A illustrates a substantially rectangular fixation wing 52, and 4B illustrates a substantially wedge shaped fixation wing 54. FIG. 4C illustrates an L-shaped fixation wing 56 in which the first end 38 is part of the body 53 of the fixation wing and the second end 40 is formed on the leg 55 of the L-shaped device. FIG. 4D illustrates a T-shaped fixation wing 58 in which the first end 38 is part of the leg 57 of the T-shaped device and the second end 40 is part of the head 59 of the T-shaped device. It is understood that various alternative designs can be utilized for fixation wings. FIGS. 1 and 2 illustrate a reverse wedge design for a fixation wing in which first end 38 is slightly wider than second end 40.

FIG. 3 illustrates another embodiment of the reinforcement system 10 of the invention. As shown, reinforcement body 12 includes a peripheral flange 30 and a hook flange 34. Peripheral flange 30 and hook flange 34 each include holes 36. In addition, the structural sidewalls 26 of the reinforcement body 12 include countersinks 26. FIG. 3 also illustrates the joinder of fixation wings 54 and 58 to peripheral flange 30. Although not illustrated, it is understood that if desired, an additional fixation wing, of a desired size and shape, may be affixed to hook flange tab 34.

As illustrated in FIG. 5, a reinforcement body 12, having a closed dome end 13 is mounted within the acetabulum 15. A bone screw 46 initially secures the reinforcement body within the acetabulum. Fixation wings 20 are joined to the flange portion 18 of the reinforcement body and are affixed to the ilium 60 and pubis 62 through bone screws 46.

Figure 6:
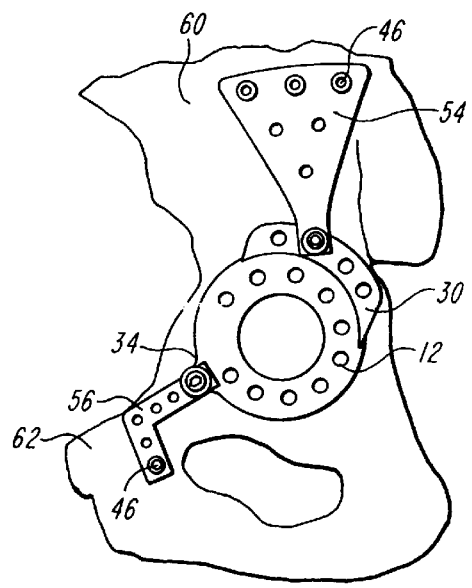
FIG. 6 is a front view of a modular acetabular system of the invention mounted within the acetabulum.

FIG. 6 further illustrates a reinforcement body 12 mounted within the acetabulum. As shown, fixation wing 54 is affixed to peripheral flange 30, and bone screws 46 secure the peripheral flange to the ilium 60. As illustrated fixation wing 56 is secured to hook flange 34 and fixation wing 56 is secured to the pubis 62 by bone screw 46.

The reinforcement system of the invention preferably is made of a biocompatible metallic material. The reinforcement body 12, fixation wings 20 and fixation elements 22 preferably are made of a soft, malleable metal that enables a surgeon to manipulate these components during surgery, if necessary, to properly conform them to a patient's anatomy. One exemplary material includes commercially pure titanium metal. Alternatively, fixation elements 22, like bone screws 46 and rivets 23, can be made of known biologically compatible metals or metal alloys including titanium alloys, cobalt-chromium alloys and stainless steel.

The use of the reinforcement system of the invention will be readily apparent to one having ordinary skill in the art. Briefly, however, the patient's acetabulum is prepared in a known manner, and the reinforcement body 12 is positioned therein in a desired orientation. The reinforcement body can be initially secured or stabilized within the acetabulum through the use of one or more bone screws or bone cement. If necessary, the flange portion, as well as other portions of reinforcement body 12 can be manipulated (i.e., deformed) to achieve a desired fit or position with respect to the patient's anatomy. The surgeon can then select the appropriate size and shape of fixation wing to be used, as well as the dimensions of the fixation wing. The fixation wings can then be secured to the reinforcement body in desired locations of flange portion 18 through the appropriate fastening technique. Any manipulation of the fixation wings to achieve appropriate fit can be accomplished by deforming or altering (i.e., cutting) the fixation wings, and the fixation wings are then secured to desired areas of the pelvis through one or more bone screws.

The fixation wings can vary in size as required by a patient's anatomy. Generally, the fixation wings have a length of about 20 to 70 mm and a width of about 10 to 70 mm. One of ordinary skill in the art can readily determine the appropriate dimensions to be assumed by the fixation wings.

It will be apparent to those of ordinary skill in the art that an important advantage of the invention is that the reinforcement system provides added flexibility to a surgeon. The surgeon can select from among a variety of fixation wings, having different sizes and shapes, and mount these fixation wings at an appropriate location on the reinforcement body. Variations in the surgical technique used to implant the reinforcement body of the invention are anticipated as well. It is understood that various modifications may be made to the invention without departing from the scope thereof. All references cited herein are expressly incorporated by reference in their entirety.

What is claimed is:

1. A modular acetabular reinforcement system, comprising:
   a metallic reinforcement body having dome and rim ends, and at least one integrally formed metallic peripheral flange portion extending along at least a portion of a perimeter of the rim end of the metallic reinforcement body;
   at least one fixation wing, each of the at least one fixation wing being removably attached to the integral flange portion of the reinforcement body and each of the at least one wing having a first end attachable to integral flange portion of the reinforcement body and an opposed, second end; and
   at least one bone fixation hole disposed in each of the at least one fixation wing.

2. The system of claim 1 wherein the reinforcement body further comprises at least one peripheral flange portion extending along at least a portion of a perimeter of the rim end.

3. The system of claim 2 wherein the reinforcement body includes an outer, bone-engaging surface and an opposed inner surface, the outer bone-engaging surface being adapted to mount within the natural acetabulum of a patient.

4. The system of claim 3 wherein the rim and dome ends are each open.

5. The system of claim 4 wherein the rim end has a diameter that is greater than the dome end.

6. The system of claim 1 wherein at least one bone fixation hole is disposed in the reinforcement body.

7. The system of claim 6 wherein the at least one bone fixation hole is a screw hole.

8. The system of claim 7 further comprising one or more fixation elements effective to affix the reinforcement body within the acetabulum.

9. The system of claim 2 wherein at least one flange fixation hole is disposed in the flange portion.

10. The system of claim 9 further comprising one or more fixation elements that cooperate with the at least one flange fixation hole to selectively join each of the at least one fixation wings to the flange portion of the reinforcement body.

11. The system of claim 1 wherein a plurality of bone fixation holes are disposed along the length of each of the at least one fixation wing, the bone fixation holes being effective to assist in securing each of the at least one fixation wing to pelvic bone.

12. The system of claim 11 further comprising a plurality of bone screws which, in cooperation with the at least one bone fixation hole, secure the at least one fixation wing to pelvic bone.

13. The system of claim 12 wherein each of the at least one fixation wing are of a structure in which the first end is narrower than the second end.

14. The system of claim 12 wherein each of the at least one fixation wing are substantially L-shaped such that the second end of each fixation wing includes a segment that extends substantially orthogonally to the first end of the fixation wing.

15. The system of claim 12 wherein each of the at least one fixation wing are substantially T-shaped, wherein a leg portion represents the first end and a head portion represents the second end.

16. The system of claim 12 wherein each of the at least one fixation wing are rectangular.

17. The system of claim 1 wherein the length of each of the at least one fixation wing is in the range of about 20 to 70 mm.

18. The system of claim 1 further comprising a means for attaching each of the at least one fixation wing to the flange portion of the reinforcement body.

19. The system of claim 1 wherein the flange portion is discontinuous.

20. A modular acetabular reinforcement system, comprising:
   a substantially cup-shaped reinforcement body having a first end mountable within a patient's acetabulum and an opposed second end mountable adjacent a lip of the acetabulum, the second end including an integrally formed flange portion extending along at least a portion of a perimeter thereof;
   a plurality of removable fixation wings, each fixation wing being selectively attached to the reinforcement body and having a first end attachable to the integrally formed flange portion of the fixation body and an opposed, second end attachable to bone;
   means for selectively affixing the first end of at least one of the fixation wings to the flange;
   at least one bone fixation hole disposed between the first and second ends of the fixation wing; and
   at least one bone fixation element for affixing the second end of the fixation wing to pelvic bone.

21. The system of claim 20 further comprising one or more bone fixation holes disposed in the reinforcement body, and one or more bone screws insertable within the at least one bone fixation holes to secure the reinforcement body within a patient's acetabulum.

22. The system of claim 20 wherein the first and second ends of the reinforcement body are open ends.

23. The system of claim 20 wherein the means for selectively affixing comprises rivets.

24. The system of claim 20 wherein the means for selectively affixing comprises threaded fixation elements.

* * * * *